US United States Patent [19]

Pasternak et al.

[11] Patent Number: 4,910,344

[45] Date of Patent: Mar. 20, 1990

[54] TREATMENT OF COMPOSITIONS CONTAINING WATER AND ORGANIC OXYGENATES

[75] Inventors: Mordechai Pasternak, Spring Valley; Craig R. Bartels; John Reale, Jr., both of Wappingers Falls, all of N.Y.

[73] Assignee: Texaco Inc., White Plains, N.Y.

[21] Appl. No.: 304,688

[22] Filed: Feb. 1, 1989

[51] Int. Cl.$^4$ .............................................. C07K 45/79
[52] U.S. Cl. .................................... 568/410; 568/411; 568/492; 568/493; 568/324; 568/913
[58] Field of Search ............... 568/913, 917, 410, 411, 568/311, 310, 492, 493, 324, 913

[56] References Cited

U.S. PATENT DOCUMENTS 2,974,178  3/1961  Hwa et al. ............................. 568/411
3,720,717  3/1973  Cox et al. .............................. 568/411

FOREIGN PATENT DOCUMENTS 0096339   5/1983  European Pat. Off. ............ 568/311
58-188829 11/1983  Japan ................................... 568/917
827474    5/1981  U.S.S.R. .............................. 568/917

OTHER PUBLICATIONS

Itoh et al, Chem. Abst, vol. 100, #157,777q (1984).
Manabe et al, Chem. Abst, vol. 19, #107358u (1983).
Hashida et al, Chem. Abst., vol. 101, #231,557g (1984).
Leeper, Chem. Abst., vol. 105, #9154d (1986).

Primary Examiner—James H. Reamer
Attorney, Agent, or Firm—Robert A. Kulason; James J. O'Loughlin; Carl G. Seutter

[57] ABSTRACT

Aqueous compositions containing organic oxygenates such as methyl isobutyl ketone are treated by pervaporation through a polyvinyl alcohol/polyacrylic acid membrane to yield retentate containing increased concentration of oxygenate.

9 Claims, No Drawings

TREATMENT OF COMPOSITIONS CONTAINING WATER AND ORGANIC OXYGENATES

RELATED APPLICATIONS

Application Ser. No. 07/214,987 filed July 5, 1988, of Mordechai Pasternak, Craig R. Bartels, and John Reale, Jr. is directed to the separation of water from a hydrocarbon mixture with an organic oxygenate by the use of membrane technology.

FIELD OF THE INVENTION

This invention relates to the dehydration of organic oxygenates such as ketones. More particularly it relates to a membrane technique for effecting separation of water from an aqueous mixture containing methyl isobutyl ketone or methyl ethyl ketone or alcohols such as isopropyl alcohol.

BACKGROUND OF THE INVENTION

As well known to those skilled in the art, it is possible to remove water from mixtures thereof with organic liquids by various techniques including adsorption or distillation. These conventional processes, particularly distillation, are however, characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, may require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the vapor pressure of the permeating species.

Illustrative membranes which have been employed in prior art techniques include those set forth in the following table:

TABLE

| Separating Layer | References |
| --- | --- |
| Nafion brand of perfluorosulfonic acid | Cabasso and Liu J. Memb. Sci. 24, 101 (1985) |
| Sulfonated polyalkylene | U.S. Pat No. 4,728,429 to Cabasso et al |
| Sulfonated polyethylene | Cabasso, Korngold & Liu J. Pol. Sc: Letters, 23, 57 (1985) |
| Fluorinated polyether | U.S. Pat. No. 4,526,948 |

TABLE-continued

| Separating Layer | References |
| --- | --- |
| or Carboxylic Acid fluorides | to Dupont as assignee of Resnickto |
| Selemion AMV brand of Asahi Glass | Wentzlaff Boddeker & Hattanbach |
| cross-linked styrene butadiene (with quaternary ammonium residues on a polyvinyl chloride backing) | J. Memb. Sci. 22,333 (1985) |
| Cellulose triacetate | Wentzlaff, Boddeker & Hattanback, J. Memb. Sci. 22, 333 (1985) |
| Polyacrylonitrile | Neel, Aptel & Clement Desalination 53, 297 (1985) |
| Crosslinked Polyvinyl Alcohol | Eur. Patent 0 096 339 to GFT as assignee of Bruschke |
| Poly(maleimide-acrylonitrile) | Yoshikawa et al J. Pol. Sci., 22,2159 (1984) |
| Dextrine-isophoronediisocyanate | Chem. Econ. Eng. Rev., 17, 34 (1985) |

The cost effectiveness of a membrane is determined by the selectivity and productivity. Of the membranes commercially available, an illustrative membrane of high performance is that disclosed in European patent 0 096 339 A2 of GFT as assignee of Bruschke—published 21 Dec. 1983.

European Patent 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of cross-linked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield ether linkages) olefinic aldehydes (which yield ether/acetal linkages), boric acid (which yields boric ester linkages), sulfonamidoaldehydes, etc.

See also J. G. Prichard, *Polyvinyl Alcohol, Basic Properties and Uses*, Gordon and Breach Science Publishers, New York (1970) or C. A. Finch, *Polyvinyl Alcohol, Properties and Applications*, John Wiley and Sons, New York (1973).

U.S. Pat. No. 4,728,429 to Cabasso et al, U.S. Pat. No. 4,067,805 to Chiang et al, U.S. Pat. No. 4,526,948 to Resnick, U.S. Pat. No. 3,750,735 to Chiang et al, and U.S. Pat. No. 4,690,766 to Linder et al provide additional background.

It is an object of this invention to provide a novel composite membrane characterized by its ability to effect separation of water from organic oxygenates such as methyl isobutyl ketone. Other objects will be apparent to those skilled in the art.

STATEMENT OF THE INVENTION

In accordance with certain of its aspects, this invention is directed to a method of separating an aqueous charge composition containing organic oxygenate which comprises maintaining a non-porous membrane separating layer of a blend of polyvinyl alcohol and an polyacrylic acid;

maintaining a pressure drop across said non-porous membrane separating layer;

passing an aqueous charge composition containing water and organic oxygenate into contact with the high pressure side of said non-porous separating layer whereby at least a portion of said water in said charge aqueous mixture and a lesser portion of organic oxygenate pass by pervaporation through said non-porous separating layer as a lean mixture containing more water and less organic oxygenate than are present in said aqueous charge and said charge is converted to a rich liquid containing less water and more organic oxygenate than are present in said aqueous charge;

recovering from the low pressure side of said non-porous separating layer said lean mixture containing more water and less organic oxygenate than are present in said aqueous charge, said lean mixture being recovered in vapor phase at a pressure below the vapor pressure thereof; and recovering from the high pressure of said non-porous separating layer said rich liquid containing a lower water content and a higher organic oxygenate content than are present in said aqueous charge.

DESCRIPTION OF THE INVENTION

The composite structure of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, non-woven fibrous polyester.

A preferred non-woven polyester carrier layer may be formulated of non-woven, thermally-bonded strands and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cuft/min/sq. ft. @0.5 inches of water.

THE POROUS SUPPORT LAYER

The porous support layer of this invention may be formed of a sheet of polymer membrane which is essentially inert with respect to (eg insoluble in) the hydrocarbon and the organic oxygenate which is used in practice of the process of this invention. The porous support layer may preferably be a membrane of polyacrylonitrile polymer. Typically the polyacrylonitrile may be of thickness of 40–80 microns, say 50 microns. The polyacrylonitrile polymers which may be employed may include those having repeating units of the formula:

THE SEPARATING LAYER

In accordance with certain of its aspects, the separating layer may be a blend or mixture of vinyl alcohol polymer and a polymer of an acrylic acid such as acrylic acid or methacrylic acid. The charge from which this separating membrane may be prepared may be an aqueous solution containing a vinyl alcohol polymer and a polymer of an acrylic acid. Typically the aqueous solution may contain 5–10 w%, say 7 w% of polyvinyl alcohol of molecular weight $M_n$ of 20,000–200,000, say 115,000 and 5–10 w%, say 7 w% of polyacrylic acid of molecular weight $M_n$ of 90,000–300,000, say 250,000. The weight ratio of vinyl alcohol polymer to acrylic acid polymer may be 0.1–10:1, say 1:1.

When the separating layer is prepared from a mixture of vinyl alcohol polymer and acrylic acid polymer (as in a preferred embodiment) it is desirable to mix the aqueous solutions of polymers to form a mix containing both polymers.

The composite membrane, prepared from the blend of polyvinyl alcohol and polyacrylic acid, may then be cured in an oven at 100° C.–225° C., say 150° C. for 1–30 minutes, say 10 minutes to yield a membrane of polyvinyl alcohol-polyacrylic acid film having a thickness of 1–10 microns, say 2 microns.

It is possible that during curing, the polyvinyl alcohol and the polyacrylic acid may crosslink or otherwise react to form ester linkages.

Illustrative polyvinyl alcohol-polyacrylic acid membranes which may be employed may include:

TABLE

I. The membrane prepared by casting a mixture of equal parts by weight of a 7 w% solution of polyvinyl alcohol of $\overline{M}_n$ of 115,000 and a 7 w% solution of polyacrylic acid of $\overline{H}_n$ of 250,000 the mixture after casting being cured at 150° C. for 10 minutes to yield a film of about 2 microns thick.

II. The membrane prepared by mixing equal parts of a 7 w% aqueous suspension of polyvinyl alcohol of $\overline{M}_n$ of 115,000 and a 7 w% aqueous suspension of polyacrylic acid of $\overline{M}_n$ of 250,000 and casting the mixture, followed by curing at 140° C. for 15 minutes to form a film of thickness about 2.5 microns.

III. The membrane prepared by mixing equal parts of a 6 w% aqueous suspension of polyvinyl alcohol of $\overline{M}_n$ of 100,000 and a 7 w% aqueous suspension of polymethacrylic acid of $\overline{M}_n$ of 280,000 and casting the mixture followed by curing at 150° C. for 10 minutes to yield a film of thickness of about 2 microns.

THE COMPOSITE MEMBRANE

It is a feature of this invention that the composite membrane of this invention may comprise (i) an optional carrier layer, characterized by porosity and mechanical strength, for supporting a porous support layer and a separating layer, (ii) a polyacrylonitrile porous support layer of molecular weight cutoff of 20,000–40,000 and (iii) as a non-porous separating layer a blend of 5–10%, say 7 w% polyvinyl alcohol of molecular weight 20,000-200,000 and, say 115,000 and 5-10 w%, say 7 w% of polyacrylic acid of molecular weight 50,000-350,000, say 250,000.

The composite membrane of this invention may be utilized in various configurations. It is, for example, preferable utilize the composite in a plate-and-frame configuration in which separating layers may be mounted on the porous support layer with the carrier layer.

It is possible to utilize a spiral wound module which includes a non-porous separating layer membrane mounted on a porous support layer and carrier layer, the assembly being typically folded and bonded or sealed along all the edges but an open edge—to form a bag-like unit which preferably has the separating layer on the outside. A cloth spacer, serving as the membrane or discharge channel is placed within the bag-like unit. The discharge channel projects from the open end of the unit.

There is then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the performations of the conduit; and the bag-like unit is wrapped around the conduit to form a spiral wound configuration.

It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell (in manner comparable to a shell-and-tube heat exchanger) provided with an inlet at one end and an outlet at the other. A baffle-like seal between the inner surface of the shell and the outer surface of the spiral-wound input prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system. In this embodiment, it will be apparent that the system may not include a carrier layer.

In another embodiment, it is possible to utilize the system of this invention as a tubular or hollow fibre. In this embodiment, the polyacrylonitrile porous support layer may be extruded as a fine tube with a wall thickness of typically 0.001-0.1 mm. The extruded tubes are passed through a bath of polyvinyl alcohol/polyacrylonitrile which is cured in situ. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer. In still another embodiment, the porous support layer may be omitted; and the separating layer is extruded and thereafter crosslinked and cured in situ prior to mounting in the headers.

PERVAPORATION

It is a feature of the non-porous polyvinyl alcohol-polyacrylic acid separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolved into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 5 mm. Hg.

For general background on pervaporation, note U.S. No. 4,277,344; U.S. No. 4,039,440; U.S. No. 3,926,798; U.S. No. 3,950,247; U.S. No. 4,035,291; etc.

It is a feature of the process of this invention that the novel membrane may be particularly useful in pervaporation processes for dewatering aqueous mixtures of organic oxygenates. It will be apparent to those skilled in the art that it may be desirable to separate large quantites of water from partially miscible systems as by decantation prior to utilizing the process of the invention to remove the last traces of water.

The advantages of the instant invention are more apparent when the charge liquid is a single phase homogenous aqueous solution as is the case for example with methyl isobutyl ketone (MIBK) or isopropanol. It is also a feature of this invention that it may be particularly useful to separate azeotropes such as isopropanol-water.

The charge organic oxygenates which may be treated by the process of this invention may include alcohols, glycols, acids, esters, ketones, aldehydes, etc. It will be apparent to those skilled in the art that the charge organic oxygenates used should be inert with respect to the separating membrane. Clearly a system wherein the membrane is attacked by the components of the charge liquid will not yield significant separation for any reasonable period of time. Best results may be achieved when treating alcohols (such as isopropanol) or glycols (such as ethylene glycol). Results achieved with acids are generally less satisfactory.

Illustrative alcohols may include ethanol, propanol, n-butanol, i-butanol, t-butanol, amyl alcohols, hexyl alcohols, etc.

Illustrative glycols may include ethylene glycol, propylene glycols, butylene glycol or glycol ethers such as diethylene glycol, triethylene glycol, or triols, including glycerine; etc.

Illustrative acids may include formic acid, oxalic acid, acetic acid, propionic acid, etc.

Illustrative esters may include ethyl acetate, methyl acetate, butyl acetate, methyl benzoate, ethylene glycol mono acetate, propylene glycol monostearate, etc.

Illustrative ethers may include tetrahydroforan, diethyl ether, and diisopropyl ether.

Illustrative ketones may include acetone, methyl ethyl ketone, methyl isobutyl ketone, acetophenone, etc.

Illustrative aldehydes may include formaldehyde, acetaldehyde, propionaldehyde, etc.

It is belived that the advantages of this invention are most apparent where the organic oxygenate is a liquid such as methyl isobutyl ketone which in preparation or in use may pick up quantites of water from various sources. For example in solvent dewaxing, water may be introduced in the MIBK, the charge lube stock, during steam distillation, etc.

A typical charge may be an aqueous mixture containing 70%–99%, say about 97 w% methyl isobutyl ketone.

In practice of the pervaporation process of this invention, the charge aqueous organic oxygenate solution typically at 40° C.–90° C., say 65° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 2–50 preferably 5–20, say 5 mm. Hg.

The permeate which passes through the membrane includes water and a small proportion of the organic oxygenate form the charge liquid. Typically, the permeate contains 96–99.9, say 99 w% water. Permeate is recovered in vapor phase.

Pervaporation may typically be carried out at a flux of 0.1–1 say 0.58 kilograms per square meter per hour (kmh). Typically, the units may show good separation (measured in terms of w% organic oxygenate in the permeate during pervaporartion of an aqueous solution of organic oxygenate through a polyvinyl alcohol separating layer.

The Separation Factor S or Sep which represents the ability of the membrane to separate water is calculated as follows:

$$S = \frac{\left(\frac{X_n}{X_m}\right)_p}{\left(\frac{X_n}{X_m}\right)_f}$$

wherein $X_n$ and $X_m$ are the weight fractions of water and non-aqueous components respectively in the permeate (P) and the feed (F). A system showing no separation at all would have a Separation Factor of 1; and a system showing perfect 100% separation would have a Separation Factor of infinity. The process of the instant invention may have a Separation Factor of as high as 70,000, typically several hundred up to 70,000, say about 62,000. Satisfactory operation may require a Separation Factor of at least about 1000 (this may vary substantially) although good commercial practice may require Separation Factors which are higher. The process of this invention tyically yields Separation Factors which are satisfactory.

Practice of the process of this invention will be apparent to those skilled in the art from inspection of the following examples wherein, as elsewhere in this specification, all parts are parts by weight unless otherwise stated. As asterisk indicates a control example.

DESCRIPTION OF SPECIFIC EMBODIMENTS

Example I

In this example, which represents the best mode presently known of carrying out the process of this invention, the selective separating layer is mounted on the porous support layer of a commercially available (from Daicel Chemical Industries Ltd) composite containing a non-woven polyester backing as carrier layer, bearing as porous support layer, a microporous polyacrylonitrile ultrafiltration (DUY-L) membrane layer of molecular weight cut-off of 40,000.

The separating layer is formed by mixing equal parts by weight of (i) a 7 w% aqueous solution of polyvinyl alcohol PVA of molecular weight $\overline{M}_n$ of 115,000 and (ii) a 7 w% aqueous solution of polyacrylic acid PAA of molecular weight $\overline{M}_n$ of 250,000. The mix is spread on the support to form a film which is then cured at 150° C. for 10 minutes.

The membrane is evaluated in a pervaporation cell to which the charge is admitted at 65° C. Permeate pressure is 5 torr at liquid nitrogen temperature.

In this preferred embodiment, the charge solution contains 97.4 w% MIBK and 2.6 w% water. The permeate condenser contains an aqueous solution containing only 0.05 w% MIBK. The Flux (kmh) is 0.58. The Separation Factor is 74,886.

Example II

In this example, the procedure of Example I is carried out, except that the charge solution at 65° C. contains 98.21 w% MIBK and 1.79 w% water. The permeate condenser contains only 0.22 w% MIBK. The Flux is 0.34. The Separation Factor is 24,884.

Example III

In this example, the procedure of Example I is followed except that the weight ratio of the solutions of polymers is 2 PVA:1 PAA. Pervaporation is carried out at 50° C. The charge contain 1.09 w% water and 98.91 w% acetone. The permeate condenser contains 9.04 w% acetone and 90.96 w% water. The Flux is 0.22 and the Separation Factor is 913.

Example IV

In this example, the procedure of Example III is followed except that the weight ratio of the solutions of polymers is 1 PVA: 2 PAA. The permeate condenser contains 3.91 w% acetone and 96.09 w% water. The Flux is 0.13 and the Separation Factor is 2230.

Example V*

In this control example, the procedure of Example III is followed except that the membrane employed is the commercially available GFT 1151 membrane of Gesellschaft fur Trenntechnik. The permeate condenser contains 46.04 w% water and 53.96 w% acetone. The Flux is 0.19 and the Separation Factor is 77.

Results comparable to those attained in Examples I-II may be attained if the charge is an organic oxygenate containing water as follows:

TABLE

| Example | Organic Oxygenate | Water | |
|---------|-------------------|-------|---|
| VI | Isopropanol | 75.7% | 24.3% |
| VII | Isopropanol | 85.0% | 15% |
| VIII | Isopropanol | 95.3% | 4.7% |
| IX | Isopropanol | 98.6% | 1.4% |
| X | Ethanol | 86.93% | 13.17% |
| XI | Ethanol | 88.82% | 11.18% |
| XII | Ethanol | 89.60% | 10.40% |
| XIII | Ethanol | 91.11% | 8.99% |
| XIV | Ethanol | 92.66% | 7.34% |
| XV | Ethanol | 93.01% | 6.99% |

Example XVI-XXXIX*

In a further series of Examples, the following charge compositions were charged to a pervaporation system

| A | MIBK containing 2.6 w % water at 65° C. |
|---|---|
| B | MIBK containing 1.79 w % water at 65° C. |
| C | Acetone containing 1.09 w % water at 50° C. |
| D | Acetone containing 2.49 w % water at 50° C. |
| E | MEK containing 2.92 w % water at 60° C. |
| F | MEK containing 1.55 w % water at 60° C. |
| G | IPA containing 2.59 w % water at 70° C. |
| H | IPA containing 1.62 w % water at 70° C. |

MIBK — methyl isobutyl ketone
MEK — methyl ethyl ketone
IPA — isopropyl alcohol

| Example | Charge | Membrane of Example | Permeate W % Water | Sep Factor | Flux kmh |
|---------|--------|---------------------|--------------------|-----------|-----------|
| XVI | A | I | 99.95 | 74,886 | 0.58 |
| XVII | B | I | 99.78 | 24,884 | 0.34 |
| XVIII | C | III | 90.96 | 913 | 0.22 |
| XIX | C | IV | 96.09 | 2230 | 0.13 |
| XX* | C | V | 46.04 | 77 | 0.19 |
| XXI | D | I | 76.18 | 125 | 0.06 |
| XXII | D | III | 97.1 | 1311 | 0.01 |
| XXIII | D | IV | 95.54 | 839 | 0.09 |
| XXIV* | D | V | 59.56 | 58 | 0.09 |
| XXV | E | I | 95.63 | 728 | 0.37 |
| XXVI | E | III | 94.01 | 522 | 0.1 |
| XXVII | E | IV | 97.88 | 1535 | 0.08 |
| XXVIII* | E | V | 46.25 | 29 | 0.71 |
| XXIX | F | I | 99.52 | 13169 | 0.19 |
| XXX | F | III | 99.31 | 9142 | 0.07 |
| XXXI | F | IV | 99.99 | 635,099 | 0.25 |
| XXXII* | F | V | 83.52 | 322 | 0.16 |
| XXXIII | G | I | 99.8 | 18,767 | 0.04 |
| XXXIV | G | III | 97.88 | 1736 | 0.01 |
| XXXV | G | IV | 99.3 | 5335 | 0.08 |
| XXXVI* | G | V | 91.73 | 417 | 0.05 |
| XXXVII | H | I | 98.43 | 3807 | 0.03 |
| XXXVIII | H | III | 97.49 | 2539 | 0.01 |
| XXXVIX | H | IV | 99.16 | 7169 | 0.05 |
| XXXX | H | V | 86.90 | 403 | 0.03 |

Although this invention has been illustrated by reference to specific embodiments, it will be apparent to those skilled in the art that various charges and modifications may be made which clearly fall within the scope of the invention.

We claim:

1. The method of separating a charge composition containing organic oxygenate which comprises
   maintaining a non-porous membrane separating layer of a blend of polyvinyl alcohol and a polyacrylic acid;
   maintaining a pressure drop across said non-porous membrane separating layer;
   passing an aqueous charge composition containing water and organic oxygenate into contact with the high pressure side of said non-porous separating layer whereby at least a portion of said water in said aqueous charge aqueous mixture and a lesser portion of organic oxygenate pass by pervaporation through said non-porous separating layer as a lean mixture containing more water and less organic oxygenate than are preent in said aqueous charge and said charge is converted to a rich liquid containing less water and more organic oxygenate than are present in said aqueous charge;
   recovering from the low pressure side of said non-porous separating layer said lean mixture containing more water and less organic oxygenate than are present in said aqueous charge, said lean mixture being recovered in vapor phase at a pressure below the vapor pressure thereof; and
   recovering from the high pressure side of said non-porous separating layer said rich liquid containing a lower water content and a higher organic oxygenate content than are present in said charge.

2. The method claimed in claim 1 wherein said organic oxygenate is an alcohol.

3. The method claimed in claim 1 wherein said organic oxygenate is a isopropyl alcohol.

4. The method claimed in claim 1 wherein said organic oxygenate is a ketone.

5. The method claimed in claim 1 wherein said organic oxygenate is methyl ethyl ketone.

6. The method claimed in claim 1 wherein said organic oxygenate is methyl isobutyl ketone.

7. The method claimed in claim 1 wherein said organic oxygenate is acetone.

8. The method claimed in claim 1 wherein said non-porous layer is prepared by casting polyvinyl alcohol and polyacrylic acid from aqueous medium as a film and curing said film at 100° C.-225° C. for 1-30 minutes.

9. The method of separating an aqueous charge composition containing methyl isobutyl ketone which comprises
   maintaining a non-porous membrane separating layer of a blend of polyvinyl alcohol and a polyacrylic acid;
   maintaining a pressure drop across said non-porous membrane separating layer;
   passing an aqueous charge composition containing water and methyl isobutyl ketone into contact with the high pressure side of said non-porous separating layer whereby at least a portion of said water in said aqueous charge aqueous mixture and a lesser portion of methyl isobutyl ketone pass by pervaporation through said non-porous separating layer as a lean mixture containing more water and less methyl isobutyl ketone than are present in said aqueous charge and said charge is converted to a rich liquid containing less water and more methyl isobutyl ketone than are present in said aqueous charge;
   recovering from the low pressure side of said non-porous separating layer said lean mixture containing more water and less methyl isobutyl ketone than are present in said aqueous charge, said lean mixture being recovered in vapor phase at a pressure below the vapor pressure thereof; and
   recovering form the high pressure side of said non-porous separating layer said rich liquid containing a lower water content and a higher methyl isobutyl ketone content than are present in said aqueous charge.

* * * * *